US00PP28758P3

(12) United States Plant Patent
Wood

(10) Patent No.: US PP28,758 P3
(45) Date of Patent: Dec. 12, 2017

(54) ***HYDRANGEA* PLANT NAMED 'SMHPMWMH'**

(50) Latin Name: *Hydrangea paniculata*
Varietal Denomination: SMHPMWMH

(71) Applicant: Timothy Wood, Spring Lake, MI (US)

(72) Inventor: Timothy Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 24 days.

(21) Appl. No.: 14/998,610

(22) Filed: Jan. 20, 2016

(65) Prior Publication Data

US 2017/0208718 P1 Jul. 20, 2017

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Cassandra Bright

(57) ABSTRACT

A new and distinct *Hydrangea* cultivar named 'SMHPMWMH' is disclosed, characterized by full mophead inflorescence, strong stems and upright habit. The new variety is a *Hydrangea*, normally produced as an ornamental plant for containers or gardens.

1 Drawing Sheet

Latin name of the genus and species: *Hydrangea paniculata.*

Variety denomination: 'SMHPMWMH'.

BACKGROUND OF THE INVENTION

The new *Hydrangea* cultivar is a product of a planned breeding program conducted by the inventor, Timothy Wood, in Grand Haven, Mich. The objective of the breeding program was to produce new *Hydrangea* varieties for garden use. The open pollination resulting in this new variety was made during July of 2008.

The seed parent is the unpatented commercial variety *Hydrangea paniculata* 'SMNHPRZEP'. The pollen parent is unknown, as it was an open pollination breeding program. The new variety was identified as a potentially interesting selection June of 2010, at a greenhouse in Grand Haven, Mich.

Asexual reproduction of the new cultivar 'SMHPMWMH' by softwood cuttings was first performed during the July of 2010, at commercial greenhouse in Grand Haven, Mich. Subsequent propagation has shown that the unique features of this cultivar are stable and reproduced true to type in 3 successive generations.

SUMMARY OF THE INVENTION

The cultivar 'SMHPMWMH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMHPMWMH' These characteristics in combination distinguish 'SMHPMWMH' as a new and distinct *Hydrangea* cultivar:

1. Full mophead inflorescence.
2. Strong stems
3. Upright habit.

PARENT COMPARISON

Plants of the new cultivar 'SMHPMWMH' are similar to plants of the unpatented seed parent, *Hydrangea paniculata* 'SMNHPRZEP' in most horticultural characteristics, however, plants of the new cultivar 'SMHPMWMH' differ in the following:

1. Earlier to change to pink.

Pollen parent unknown as this is product of open pollination.

COMMERCIAL COMPARISON

'SMHPMWMH' can be compared to the patented commercial variety *Hydrangea paniculata* 'SMHPPINO' U.S. Plant Pat. No. 27,302. These varieties are similar in most horticultural characteristics; however 'SMHPMWMH' differs in the following:

1. The comparator has a larger inflorescence.
2. Strong flowering stems. The comparator has strong stems, but falls under weight of large inflorescence.
3. White sepals. The comparator has light green/white sepal.

BRIEF DESCRIPTION OF THE PHOTOGRAPH

The accompanying photograph in FIG. 1 illustrates in full color a typical plant of 'SMHPMWMH' grown in a field, in Grand Haven, Mich., USA. Age of the plant photographed is approximately 3 years.

The photograph was taken using conventional techniques and although colors may appear different from actual colors due to light reflectance it is as accurate as possible by conventional photographic techniques.

DETAILED BOTANICAL DESCRIPTION

In the following description, color references are made to The 2015 Royal Horticultural Society Colour Chart except where general terms of ordinary dictionary significance are used. The following observations and measurements describe 'SMHPMWMH' plants grown in a field, in Grand Haven, Mich., USA. The growing temperature ranged from approximately 18° C. to 27° C. daytime and 5° to 10° C. at night. Measurements and numerical values represent averages of typical plant types. Measurements were taken during July of 2015.

Botanical classification: *Hydrangea paniculata* 'SMHPMWMH.'

PROPAGATION

Time to initiate roots: Approximately 18 days at approximately 24° C.

Time to produce a rooted young plants: Approximately 60 days at approximately 24° C.

Root description: Thin to thick, moderate to dense, freely root branching, fleshy. Color is white and brown.

Propagation method: Softwood cuttings.

PLANT

Age of plant described: 3 years.

Pot size: Field grown.

Growth habit: Flowering perennial shrub, upright.

Overall plant shape: Upright/mounded.

Height: 95 cm.

Plant spread: 80 cm.

Growth rate: Good.

Plant vigor: Good.

Branching characteristics: Upright/outward basal branches, some pinching required.

Length of lateral branches: 80 cm.

Number of lateral branches: 25.

Diameter of lateral branches: 0.5-1 cm.

Lateral branch shape and appearance: Rounded and slightly wooded.

Lateral branch strength: Strong, rigid.

Internode length: 3-4 cm.

Branch color:

*Immature*.—Near RHS Greyed-green 194B with overlay of Greyed-brown 199A.

*Mature*.—Near RHS Brown Greyed-brown 199B.

Branch aspect: 0-35°.

Branch pubescence: Yes, more prevalent on newer growth.

FOLIAGE

Leaf:

*Arrangement*.—Opposite.

*Average length*.—New: 9.1 cm. Mature: 13.1 cm.

*Average width*.—New: 5.2 cm. Mature: 6.8 cm.

*Shape of blade*.—Ovate.

*Apex*.—Acuminate.

*Base*.—Obtuse to Cuneate.

*Margin*.—Serrulate and softly undulate.

*Texture and appearance of top surface*.—New: Smooth, coriaceous. Mature: Slightly pubescent, scabrous, rugose.

*Texture and appearance of bottom surface*.—New: Smooth and rugose. Mature: Slightly pubescent, rugose.

*Leaf pubescence*.—Slightly on underside of mature leaf.

*Color*.—Young foliage upper side: Near RHS Green 138A. Young foliage under side: Near RHS Green 138B. Mature foliage upper side: Near RHS Green 137A. Mature foliage under side: Near RHS Green 138B.

*Venation*.—Type: Pinnate. Venation color upper side: Near RHS Yellow-green 145A. Venation color under side: Near Yellow-Green 145C.

Petiole:

*Average length*.—1.5 to 2 cm.

*Diameter*.—2 mm.

*Color*.—Upper side: Near RHS Yellow-green 145A. Under side: Near RHA Yellow-green 145C.

*Texture upper side*.—Smooth, coriaceous.

*Texture under side*.—Smoot, coriaceous, slightly pubescent.

FLOWER

Bloom period:

*Natural season*.—Mid-Summer through Fall.

Inflorescence:

*Type*.—Mophead.

*Quantity of flowers per inflorescence*.—Fertile flowers, 65. Sterile Flowers, 1000's.

*Persistent or self-cleaning*.—Persistent.

*Fragrance*.—Slight-Fresh/floral.

Panicle:

*Shape*.—Corymb to cyme.

*Height*.—22 cm.

*Diameter*.—17 cm.

Sterile flower:

*Androecium*.—Yes.

*Bud shape*.—Orbicular and lobed.

*Bud length*.—1 mm.

*Bud diameter*.—1 mm.

*Bud color*.—Near RHS White NN155B.

*Flower aspect*.—Upright and outward.

*Flower shape*.—Whorled.

*Flower length*.—2 to 2.5 cm.

*Flower diameter*.—2 to 2.5 mm.

*Flower depth*.—1 cm.

Sterile flower petals:

*Petal arrangement*.—Whorled.

*Length of petal*.—1.5 mm.

*Width of petal*.—1 mm.

*Apex*.—Obtuse.

*Shape of petal*.—Elliptic to obtuse.

*Petal margin*.—Entire.

*Petal base*.—Rounded to slightly acute.

*Petal number*.—4.

*Petal texture*.—Smooth, glabrous, upper and under side.

*Color*.—Upper surface at first opening: Near RHS White NN155B. Upper surface at maturity: Near RHS White NN155B. Under surface at first opening: Near RHS White NN155B. Under surface at maturity: Near RHS White NN155B.

Sterile flower sepal:

*Arrangement*.—Whorl.

*Number*.—4.

*Shape*.—Elliptic to obtuse.

*Tip*.—Obtuse.

*Base*.—Rounded to slightly acute.

*Margin*.—Entire.

*Length.*—1.4 cm.
*Width.*—1 cm.
*Texture, upper.*—Smooth, glabrous.
*Texture, lower.*—Smooth, glabrous.
*Color.*—Upper surface at first opening: Near RHS White NN155B. Upper surface at maturity: Near RHS White NN155B then turning to Greyed-purple 186D. Under surface at first opening: Near RHS White NN155B. Under surface at maturity: Near RHS White NN155B with slight highlighting of Greyed-purple 186D. Fading to Upper surface: Near RHS Yellow-green 145A. Fading to Under surface: Near RHS Yellow-green 145A.

Sterile flower pedicel:
*Length.*—1 cm.
*Diameter.*—1.5 cm.
*Angle.*—0-45°.
*Strength.*—Good.
*Texture.*—Smooth, slightly pubescent.
*Color.*—Near RHS Yellow-green 145A.

Fertile flower:
*Bud shape.*—Orbicular and lobed.
*Bud length.*—2 mm.
*Bud diameter.*—1.5 mm.
*Bud color.*—Near RHS White NN155B.
*Flower aspect.*—Upright and outward.
*Flower shape.*—Orbicular and lobed.
*Flower length.*—2.5 mm.
*Flower diameter.*—2.5 mm.
*Flower depth.*—1 cm.

Fertile flower petals:
*Length of petal.*—1 mm.
*Width of petal.*—1.25 mm.
*Apex.*—Acute.
*Shape of petal.*—Ovate.
*Petal margin.*—Entire.
*Petal arrangement.*—Whorl.
*Petal number.*—5.
*Petal base.*—Obtuse.
*Petal texture.*—Smooth, glabrous, upper and under side.
*Color.*—Upper surface at first opening: Near RHS White NN155B. Upper surface at maturity: Near RHS White NN155B. Under surface at first opening. Near RHS White NN155B. Under surface at maturity: Near RHS White NN155B. Upper surface fading to: Near RHS White NN155B. Lower surface fading to: Near RHS White NN155B.

Fertile flower pedicel:
*Angle.*—Range of 15-90° from attachment.
*Strength.*—Strong.
*Length.*—2.5 mm.
*Width.*—0.5 mm.
*Texture.*—Smooth, slightly pubescent.
*Color.*—Near RHS Yellow-green 145A.

Fertile flower sepal:
*Arrangement.*—Ungulate.
*Number.*—5.
*Shape.*—Fused/inconspicuous.
*Tip.*—Acute.
*Base.*—Rounded to obtuse.
*Margin.*—Entire.
*Length.*—Less than 1 mm.
*Width.*—Less than 1 mm.
*Texture, upper.*—Smooth, glabrous.
*Texture, lower.*—Smooth, glabrous.
*Color.*—Upper surface at first opening: Near RHS Yellow-green 145A. Upper surface at maturity: Near RHS Yellow-green 145A. Under surface at first opening: Near RHS Yellow-green 145A. Under surface at maturity: Near RHS Yellow-green 145A. Upper surface fading to: Near RHS Yellow-green 145A. Lower surface fading to: Near RHS Yellow-green 145A.

REPRODUCTIVE ORGANS

Sterile flower:
*Stamen number.*—5.
*Filament length.*—0.75 mm.
*Filament color.*—Near RHS White NN155B.
*Anther shape.*—Liner.
*Anther color.*—Near RHS White NN155B.
*Anther length.*—1 mm.
*Pollen amount.*—Some.
*Pollen color.*—Near RHS White NN155B.
*Gynoecium.*—Yes.
*Pistil number.*—1.
*Pistil length.*—1 mm.
*Stigma shape.*—Club.
*Style length.*—0.75 mm.
*Style color.*—Near RHS White NN155B.
*Ovary color.*—Near RHS White NN155B.

Fertile flower:
*Stamen number.*—5.
*Filament length.*—0.75 mm.
*Filament color.*—Near RHS Yellow-green 145A.
*Anther shape.*—Liner.
*Anther length.*—1 mm.
*Anther color.*—Near RHS White NN155B.
*Pollen amount.*—Some.
*Pollen color.*—Near RHS White 155B.
*Pistil number.*—1.
*Pistil length.*—1 mm.
*Stigma shape.*—Club.
*Stigma color.*—Near RHS White NN155B.
*Style length.*—0.75 mm.
*Style color.*—Near RHS White NN155B.

OTHER CHARACTERISTICS

Disease resistance: Neither resistance nor susceptibility to diseases or pests has been observed in this variety.
Cold tolerance: −32° C. to 36° C.
Fruit/seed production: 1000's of seeds produced. Abundant, minute seed produced. Seed less than 1 mm in diameter and length, brown, too small to accurately measure with R.H.S. chart.
Other traits: Very good resistance to sunburn or sun scald. Strong stems tolerant to wind. Flowers hold well making them tolerant to rain.

What is claimed is:

1. A new and distinct cultivar of *Hydrangea* plant named 'SMHPMWMH' as herein illustrated and described.

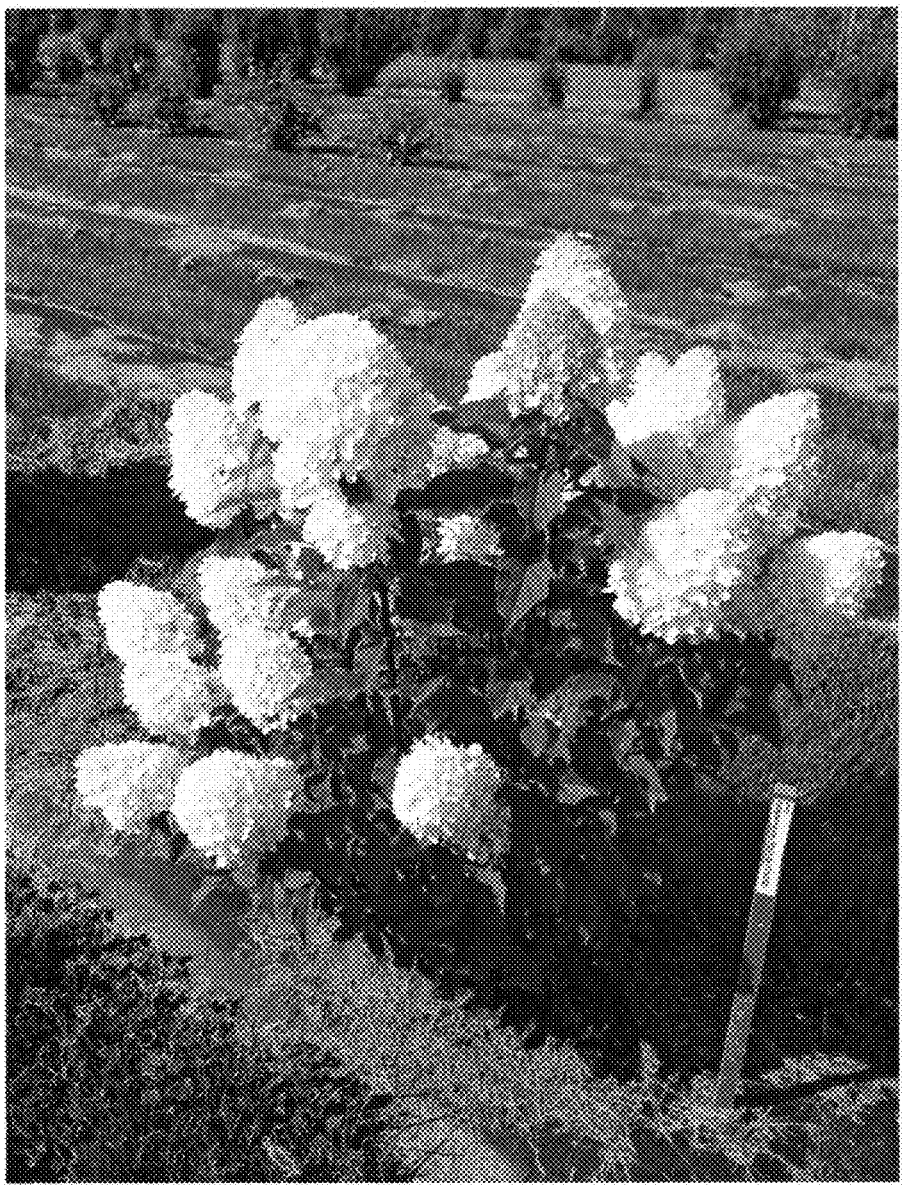

* * * * *